(12) United States Patent
Slayton

(10) Patent No.: US 10,898,735 B2
(45) Date of Patent: *Jan. 26, 2021

(54) SYSTEMS AND METHODS FOR ACCELERATING HEALING OF IMPLANTED MATERIAL AND/OR NATIVE TISSUE

(71) Applicant: Guided Therapy Systems, LLC, Mesa, AZ (US)

(72) Inventor: Michael H. Slayton, Tempe, AZ (US)

(73) Assignee: Guided Therapy Systems, LLC, Scottsdale, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/231,438

(22) Filed: Dec. 22, 2018

(65) Prior Publication Data

US 2019/0143148 A1 May 16, 2019

Related U.S. Application Data

(60) Continuation of application No. 15/246,199, filed on Aug. 24, 2016, now Pat. No. 10,166,411, which is a division of application No. 13/545,953, filed on Jul. 10, 2012, now Pat. No. 9,452,302.

(60) Provisional application No. 61/506,127, filed on Jul. 10, 2011, provisional application No. 61/506,126, filed on Jul. 10, 2011, provisional application No. 61/506,160, filed on Jul. 10, 2011, provisional application No. 61/506,163, filed on Jul. 10, 2011, provisional application No. 61/506,125, filed on Jul. 10, 2011, provisional application No. 61/506,610, filed on Jul. 11, 2011, provisional application No. 61/506,609, filed on Jul. 11, 2011.

(51) Int. Cl.
| A61N 7/00 | (2006.01) |
| A61N 7/02 | (2006.01) |
| A61B 18/18 | (2006.01) |
| A61M 37/00 | (2006.01) |
| A61B 18/00 | (2006.01) |

(52) U.S. Cl.
CPC ................. *A61N 7/00* (2013.01); *A61N 7/02* (2013.01); *A61B 18/18* (2013.01); *A61B 2018/00642* (2013.01); *A61M 37/0092* (2013.01); *A61N 2007/0004* (2013.01); *A61N 2007/006* (2013.01); *A61N 2007/0017* (2013.01); *A61N 2007/0034* (2013.01); *A61N 2007/0039* (2013.01); *A61N 2007/0052* (2013.01); *A61N 2007/0073* (2013.01); *A61N 2007/0078* (2013.01); *A61N 2007/027* (2013.01)

(58) Field of Classification Search
CPC ....... A61B 18/18; A61M 37/0092; A61N 7/02
See application file for complete search history.

(56) References Cited

U.S. PATENT DOCUMENTS

| 8,486,001 B2 * | 7/2013 | Weyant | A61H 23/0245 601/1 |
| 2011/0040213 A1 * | 2/2011 | Dietz | A61N 7/00 601/2 |

* cited by examiner

*Primary Examiner* — Rex R Holmes
(74) *Attorney, Agent, or Firm* — Quarles & Brady LLP

(57) ABSTRACT

Various embodiments provide methods and systems for ultrasound treatment of tissue are provided. Accordingly, a method can include locating an implant in a site in a body, directing a medicant to at least one of the implant and the site, directing ultrasound energy to the site, and accelerating healing of the implant and/or native tissue at the site.

8 Claims, 9 Drawing Sheets

SYSTEMS AND METHODS FOR ACCELERATING HEALING OF IMPLANTED MATERIAL AND/OR NATIVE TISSUE

CROSS-REFERENCE TO RELATED APPLICATIONS

This application is a continuation of U.S. patent application Ser. No. 15/246,199 filed Aug. 24, 2016, which is a divisional of U.S. patent application Ser. No. 13/545,953 filed Jul. 10, 2012, now U.S. Pat. No. 9,452,302, which claims priority to and the benefit of U.S. Provisional Patent Application 61/506,125, entitled "Systems and Methods for Creating Shaped Lesions" filed Jul. 10, 2011; U.S. Provisional Patent Application 61/506,127, entitled "Systems and Methods for Treating Injuries to Joints and Connective Tissue," filed Jul. 10, 2011; U.S. Provisional Patent Application 61/506,126, entitled "System and Methods for Accelerating Healing of Implanted Materials and/or Native Tissue," filed Jul. 10, 2011; U.S. Provisional Patent Application 61/506,160, entitled "Systems and Methods for Cosmetic Rejuvenation," filed Jul. 10, 2011; U.S. Provisional Patent Application 61/506,163, entitled "Methods and Systems for Ultrasound Treatment," filed Jul. 10, 2011; U.S. Provisional Patent Application 61/506,609, entitled "Systems and Methods for Monitoring Ultrasound Power Efficiency," filed Jul. 11, 2011; and U.S. Provisional Patent Application 61/506,610, entitled "Methods and Systems for Controlling Acoustic Energy Deposition into a Medium," filed Jul. 11, 2011; all of which are incorporated by reference herein.

BACKGROUND

Medical implants are a common treatment for a patient's various ailments. Examples of an implant can include mesh, scaffold, a screw, a bone graph, a pin, a plate, a rod, and/or a stent. Joint replacements have become popular implants for older patients. Cosmetic implants, such as, breast implants, fillers, and facial implants continue to grow in popularity. For many patients, recovery from an implant surgery can be long and difficult healing process. In some cases, the body of the patient rejects the implant. Accordingly, new approaches to integrating an implant into tissue and/or bone are needed.

SUMMARY

Various embodiments, described herein, provide methods and systems for ultrasound treatment of tissue. Accordingly, a method can include locating an implant in a site in a body, directing a medicant to at least one of the implant and the site, directing ultrasound energy to the site, and accelerating healing of the implant and/or native tissue at the site.

Various embodiments described herein, provide a method for treating an implant in a region of interest of a body. In some embodiments the method comprises targeting a region of interest comprising an implant and tissue surrounding the implant and imaging the implant in the region of interest. In addition, the method can comprise delivering ultrasound energy to the implant, creating a conformal region of elevated temperature in the region of interest, and initiating at least one thermally induced biological effect in the region of interest.

Various embodiments provide a method of treating an implant in a region of interest. In some embodiments, the method can comprise targeting an implant comprising a biological material and the implant is located in a region of interest comprising tissue. In some embodiments, the method can comprise directing ultrasound energy to the implant comprising the biological material, effecting the biological material with the ultrasound energy, and creating a therapeutic effect the tissue in the region of interest with the biological material.

Various embodiments provide a method of enhancing a cosmetic implant. In some embodiments, the method can comprise targeting a location of the cosmetic implant in a patient, determining an enhancement necessary to improve an aesthetic of the cosmetic implant, delivering ultrasound energy to at least one of the cosmetic implant and tissue surrounding the cosmetic implant, and improving an aesthetic of the cosmetic implant with the ultrasound energy.

DRAWINGS

The present disclosure will become more fully understood from the detailed description and the accompanying drawings, wherein.

DESCRIPTION

Figure 1:
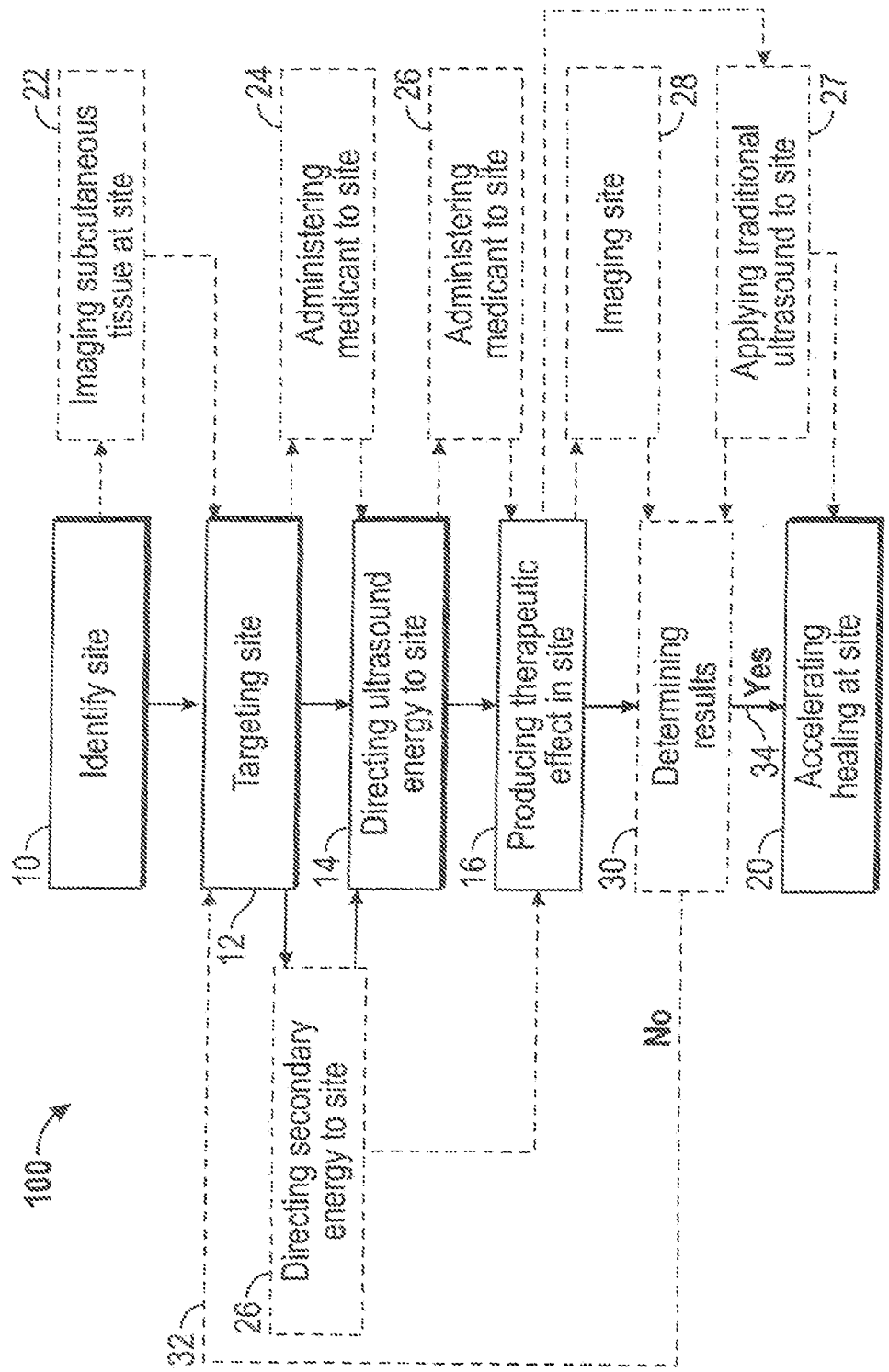
FIG. 1 is a flow chart illustrating various methods, according to various non-limiting embodiments.

The following description is in no way intended to limit the various embodiments, their application, or uses. As used herein, the phrase "at least one of A, B, and C" should be construed to mean a logical (A or B or C), using a non-exclusive logical "or," As used herein, the phrase "A, B and/or C" should be construed to mean (A, B, and C) or alternatively (A or B or C), using a non-exclusive logical "or." It should be understood that steps within a method may be executed in different order without altering the principles of the present disclosure.

The drawings described herein are for illustrative purposes only of selected embodiments and not all possible implementations, and are not intended to limit the scope of any of the various embodiments disclosed herein or any equivalents thereof. It is understood that the drawings are not drawn to scale. For purposes of clarity, the same reference numbers will be used in the drawings to identify similar elements.

The various embodiments may be described herein in terms of various functional components and processing steps. It should be appreciated that such components and steps may be realized by any number of hardware components configured to perform the specified functions. For example, various embodiments may employ various medical treatment devices, visual imaging and display devices, input terminals and the like, which may carry out a variety of functions under the control of one or more control systems or other control devices. In addition, the embodiments may be practiced in any number of medical contexts and that the various embodiments relating to a method and system for acoustic tissue treatment as described herein are merely indicative of examples of applications. For example, the principles, features and methods discussed may be applied to any medical application. Further, various aspects of the various embodiments may be suitably applied to cosmetic applications. Moreover, some of the embodiments may be applied to cosmetic enhancement of skin and/or various soft tissue layers.

Various embodiments described herein, provide a method for treating an implant in a region of interest of a body. In some embodiments the method comprises targeting a region of interest comprising an implant and tissue surrounding the implant and imaging the implant in the region of interest; in addition, the method can comprise delivering ultrasound energy to the implant, creating a conformal region of elevated temperature in the region of interest, and initiating at least one thermally induced biological effect in the region of interest.

In some embodiments, the method can further comprise delivering a medicant to the region of interest and optionally can comprise activating the medicant in the region of interest. In some embodiments, the method can further comprise accelerating adoption of the implant by the surrounding tissue.

In some embodiments, the conformal region of elevated temperature in the region of interest can release a medicant from the implant. In some embodiments, the method can further comprise applying mechanical ultrasound energy to region of interest and delivering the medicant to the tissue surrounding the implant. In some embodiments, the delivering the medicant to the tissue surrounding the implant can minimize formation of scar tissue in the surrounding tissue. In some embodiments, the conformal region of elevated temperature in the region of interest changes the phase of the implant from a solid to a liquid and delivering the liquid to the region of interest.

In some embodiments, the method can further comprise stimulating a change to at least one of concentration and an activity of at least one of an inflammatory mediator and a growth factor. In some embodiments, the thermally induced biological effect is at least one of coagulation, increased perfusion, reduction of inflammation, generation of heat shock proteins, and initiation of healing cascade.

Various embodiments provide a method of treating an implant in a region of interest. In some embodiments, the method can comprise targeting an implant comprising a biological material and the implant is located in a region of interest comprising tissue. In some embodiments, the method can comprise directing ultrasound energy to the implant comprising the biological material, effecting the biological material with the ultrasound energy, and creating a therapeutic effect the tissue in the region of interest with the biological material.

In some embodiments, the effecting the biological material with the ultrasound energy is activating the biological material. In some embodiments, the effecting the biological material with the ultrasound energy is increasing adoption of the biological material into tissue. In some embodiments, the effecting the biological material with the ultrasound energy is potentiating the biological material.

In some embodiments, the method can further comprise creating a conformal region of elevated temperature in the tissue in the region of interest. In some embodiments, the method can further comprise further comprising creating a lesion in the tissue and stimulating a wound healing cascade in the region of interest. In some embodiments, the method can further comprise changing the phase of the biological material with the ultrasound energy. In some embodiments, the method can further comprise imaging at least one of the implant and the tissue in the region of interest.

In some embodiments, the method can further comprise directing a second energy into the region of interest and creating a second therapeutic effect in the region of interest with the second energy. In some embodiments, the second energy is one of radiofrequency energy, photon-based energy, plasma-based energy, magnetic resonance energy, microwave energy, and mechanical energy. In some embodiments, the second energy is a second ultrasound emission at a different frequency. In some embodiments, the directing the second energy into the region of interest stops the effecting the biological material. In some embodiments, the second therapeutic effect in the region of interest is one of is at least one of coagulation, increased perfusion, reduction of inflammation, generation of heat shock proteins, and initiation of healing cascade.

Various embodiments provide a method of enhancing a cosmetic implant. In some embodiments, the method can comprise targeting a location of the cosmetic implant in a patient, determining an enhancement necessary to improve an aesthetic of the cosmetic implant, delivering ultrasound energy to at least one of the cosmetic implant and tissue surrounding the cosmetic implant, and improving an aesthetic of the cosmetic implant with the ultrasound energy.

In some embodiments, the cosmetic implant is a breast implant located in a breast of the patient. In some embodiments, the improving an aesthetic of the cosmetic implant with the ultrasound energy is modifying a shape of the breast of the patient. In some embodiments, the method can further comprise creating a conformal region of elevated temperature in at least one of the breast implant and the tissue surrounding the breast implant.

In some embodiments, the method can further comprise creating at least one lesion in the tissue surrounding the breast implant, applying mechanical ultrasound energy to at least one of the breast implant and the tissue surrounding the breast implant, moving the breast implant into the space created by the at least one lesion; and modifying a shape of the breast of the patient.

In some embodiments, the cosmetic implant is a cosmetic filler located below a skin surface of the patient. In some embodiments, the method can further comprise improving an aesthetic of the cosmetic implant with the ultrasound energy is smoothing the skin surface proximate to the cosmetic filler.

In some embodiments, the method can further comprise heating the cosmetic filler with the ultrasound energy, changing physical characteristic of the cosmetic filler, applying mechanical ultrasound energy to at least one of the cosmetic filler and the tissue surrounding the cosmetic filler and below the skin surface, moving the cosmetic filler into and/or along the tissue surrounding the cosmetic filler and below the skin surface, and smoothing the skin surface proximate to the cosmetic filler.

In various embodiments, increasing a temperature at a site comprising an implant can change a phase of at least one material within the implant. For example, upon the increasing the temperature, from the delivery conformal ultrasound energy to the site, can change the phase of the implant from a solid to a liquid. For example, upon the increasing the temperature, from the delivery conformal ultrasound energy to the site, can change one material within the implant from a solid to a liquid. In some embodiments, such a liquid can be a medicant, which can then elute and/or be administered to tissue within and/or surrounding the site. In various embodiments, increasing a temperature at a site comprising an implant can cause non-linear delivery of a medicant from an implant to administered to tissue within and/or surrounding the site.

With reference to FIG. 1, a method of treatment is illustrated according to various embodiments. Step 10 is identifying the implant site ("site"). The site maybe anywhere in the body, such as, for example, in any of the following: leg, arm, wrist, hand, ankle, knee, foot, hip, shoulder, back, neck, chest, abdomen, and combinations thereof. In various embodiments, an implant is a medical device manufactured to replace a missing biological structure, support a damaged biological structure, or enhance an existing biological structure. In some embodiments, an implant is a man-made device. In some embodiments, an implant is a transplanted biomedical tissue. In some embodiments, an implant is a combination of a man-made device and transplanted biomedical tissue. In some embodiments, an implant is bioactive, such as subcutaneous drug or medicant delivery devices, such as, for example, implantable pills or drug-eluting, stents.

Next, Step 12 is targeting the site. In some embodiments, the site can be located in subcutaneous tissue or other soft tissue located below or at the skin surface of the site, which can be anywhere in the body, such as, those listed previously. In various embodiments, the site includes a muscle and connective tissue layer. The muscle and connective layer can comprise any or all of the following tissues: muscle, tendon, ligament, and cartilage. In some embodiments, the site can be located in a joint, in some embodiments, the site can be located in an organ. In some embodiments, a portion of the site can be located in one or more bones. Optionally, step 22 is imaging subcutaneous tissue at the site, which can be between steps 10 and 12 or can be substantially simultaneous with or be part of step 12.

After step 12, step 14 is directing ultrasound energy to the implant and/or native tissue at site. The ultrasound energy may be focused or unfocused. The ultrasound energy can be focused to the site. The ultrasound energy may ablate a portion of the site. The ultrasound energy may coagulate a portion of the site. The ultrasound energy can produce at least one lesion in the site. The ultrasound energy may micro-score a portion of the site. The ultrasound energy may be streaming. The ultrasound energy may be directed to a first depth and then directed to a second depth. The ultrasound energy may force a pressure gradient to site. The ultrasound energy may be cavitation. The ultrasound energy may be a first ultrasound energy effect, which comprises an ablative or a hemostatic effect, and a second ultrasound energy effect, which comprises at least one of non-thermal streaming, hydrodynamic, diathermic, and resonance induced tissue effects. Directing ultrasound energy to the site is a non-invasive technique. As such the layers above the site are spared from injury. Such treatment does not require an incision in order to reach the site to perform treatment for the injury.

In various embodiments, the ultrasound energy level directed to site and/or native tissue is in a range of about 0.1 joules to about 500 joules in order to create an ablative lesion. However, the ultrasound energy 108 level can be in a range of from about 0.1 joules to about 100 joules, or from about 1 joules to about 50 joules, or from about 0.1 joules to about 10 joules, or from about 50 joules to about 100 joules, or from about 100 joules to about 500 joules, or from about 50 joules to about 250 joules.

Further, the amount of time ultrasound energy is applied at these levels to create a lesion varies in the range from approximately 1 millisecond to several minutes. However, a range can be from about 1 millisecond to about 5 minutes, or from about 1 millisecond to about 1 minute, or from about 1 millisecond to about 30 seconds, or from about 1 millisecond to about 10 seconds, or from about 1 millisecond to about 1 second, or from about 1 millisecond to about 0.1 seconds, or about 0.1 seconds to about 10 seconds, or about 0.1 seconds to about 1 second, or from about 1 millisecond to about 200 milliseconds, or from about 1 millisecond to about 0.5 seconds.

The frequency of the ultrasound energy can be in a range from about 0.1 MHz to about 100 MHz, or from about 0.1 MHz to about 50 MHz, or from about 1 MHz to about 50 MHz or about 0.1 MHz to about 30 MHz, or from about 10 MHz to about 30 MHz, or from about 0.1 MHz to about 20 MHz, or from about 1 MHz to about 20 MHz, or from about 20 MHz to about 30 MHz.

The frequency of the ultrasound energy can be in a range from about 1 MHz to about 12 MHz, or from about 5 MHz to about 15 MHz, or from about 2 MHz to about 12 MHz or from about 3 MHz to about 7 MHz.

In some embodiments, the ultrasound energy can be emitted to depths at or below a skin surface in a range from about 0 mm to about 150 mm, or from about 0 mm to about 100 mm, or from about 0 mm to about 50 mm, or from about 0 mm to about 30 mm, or from about 0 mm to about 20 mm, or from about 0 mm to about 10 mm, or from about 0 mm to about 5 mm. In some embodiments, the ultrasound energy can be emitted to depths below a skin surface in a range from about 5 mm to about 150 mm, or from about 5 mm to about 100 mm, or from about 5 mm to about 50 mm, or from about 5 mm to about 30 mm, or from about 5 mm to about 20 mm, or from about 5 mm to about 10 mm. In some embodiments, the ultrasound energy can be emitted to depths below a skin surface in a range from about 10 mm to about 150 mm, or from about 10 mm to about 100 mm, or from about 10 mm to about 50 mm, or from about 10 mm to about 30 mm, or from about 10 mm to about 20 mm, or from about 0 mm to about 10 mm.

In some embodiments, the ultrasound energy can be emitted to depths at or below a skin surface in the range from about 20 mm to about 150 mm, or from about 20 mm to about 100 mm, or from about 20 mm to about 50 mm, or from about 20 mm to about 30 mm. In some embodiments, the ultrasound energy can be emitted to depths at or below a skin surface in a range from about 30 mm to about 150 mm, or from about 30 mm to about 100 mm, or from about 30 mm to about 50 mm. In some embodiments, the ultrasound energy can be emitted to depths at or below a skin surface in a range from about 50 mm to about 150 mm, or from about 50 mm to about 100 mm. In some embodiments, the ultrasound energy can be emitted to depths at or below a skin surface in a range from about 20 mm to about 60 mm, or from about 40 mm to about 80 mm, or from about 10 mm to about 40 mm, or from about 5 mm to about 40 mm, or from about 0 mm to about 40 mm, or from about 10 mm to about 30 mm, or from about 5 mm to about 30 mm, or from about 0 mm to about 30 mm.

In various embodiments, a temperature of site and/or native tissue receiving the ultrasound energy can be in a range from 30° C. to about 100° C., or from 43° C. to about 60° C., or from 50° C. to about 70° C., or from 30° C. to about 50° C., or from 43° C. to about 100° C., or from 33° C. to about 100° C., or from 30° C. to about 65° C., or from 33° C. to about 70° C., as well as variations thereof.

Also, depending at least in part upon the specific biological effect and tissue targeted, temperature of site and/or native tissue may increase within ROI may range from approximately 10° C. to about 15° C. In various embodiments, a temperature of site and/or native tissue receiving the ultrasound energy is raised to a temperature in the range form about 40° C. to about 55° C., or from about 43° C. to about 48° C., or below a threshold of ablation of the tissue.

Optionally, step 24, which is administering a medicant to the implant and/or native tissue at site, can be between steps 12 and 14. The medicant can be any chemical or naturally occurring substance that can assist in treating the injury. For example the medicant can be an anti-inflammant, or a steroid, or a blood vessel dilator. The medicant can be administered by applying it to the skin above the site. The medicant can be administered to the circulatory system. For example, the medicant can be in the blood stream and can be activated or moved to the site by the ultrasound energy. Any naturally occurring proteins, stem cells, growth factors and the like can be used as medicant in accordance to various embodiments. A medicant can be mixed in a coupling gel or can be used as a coupling gel. Medicants are further discussed herein.

Step 16 is producing a therapeutic effect in the site. A therapeutic effect can be cauterizing and repairing a portion of the site. A therapeutic effect can be stimulating or increase an amount of heat shock proteins. Increasing temperature of the tissue, around and/or in site, can stimulate a change to at least one of a concentration and an activity of growth factors and/or heat shock proteins in the tissue around and/or in site. Such a therapeutic effect can cause white blood cells to promote healing of a portion of the site, including, for example, implanted and/or native tissue. A therapeutic effect can be peaking inflammation in a portion of the site to decrease pain at the site. Peaking inflammation can cause suppression of the immune system around and in the site. Peaking inflammation can accelerate a healing cascade, such as, for example, the coagulation cascade.

A therapeutic effect can be creating lesion to restart or increase the wound healing cascade at the site. A therapeutic effect can be increasing the blood perfusion to the site, which can accelerate healing at the site. Such a therapeutic effect would not require ablative ultrasound energy. A therapeutic effect can be encouraging collagen growth. A therapeutic effect can be relieving pain. A therapeutic effect may increase the "wound healing" response through the liberation of cytokines and may produce reactive changes within the tendon and muscle itself, helping to limit surrounding tissue edema and decrease the inflammatory response at site. A therapeutic effect can be synergetic with the medicant administered to site in steps 24 and/or 26. A therapeutic effect can be healing implanted and/or native tissue at or near site. A therapeutic effect can be integrating implant to site. A therapeutic effect can accelerated healing at site. Therapeutic effects can be combined.

Optionally, step 26, which is administering medicant to site, can be between steps 14 and 16 or can be substantially simultaneous with or be part of step 16. The medicants useful in step 26 are essentially the same as those discussed for step 24.

Optionally, after step 12, step 25, which is directing secondary energy to the site can be substantially simultaneous with or be part of step 16. However, step 25 can be administered at least one of before and after step 16. Step 25 can be alternated with step 16, which can create a pulse of two different energy emissions to the site. Secondary energy can be provided by a laser source, or an IPL source, or a radio frequency, or a plasma source, or a magnetic resonance source. Secondary energy can be provided by any appropriate energy source now known or created in the future. More than one secondary energy source may be used for step 25.

Furthermore, various embodiments provide energy, which may be a first energy and a second energy. For example, a first energy may be followed by a second energy, either immediately or after a delay period. In another example, a first energy and a second energy can be delivered simultaneously. In some embodiments, the first energy and the second energy is ultrasound energy. In some embodiments, the first energy is ultrasound and the second energy is generated by one of a laser, an intense pulsed light, a light emitting diode, a radiofrequency generator, photon-based energy source, plasma source, a magnetic resonance source, or a mechanical energy source, such as for example, pressure, either positive or negative. In other embodiments, energy may be a first energy, second energy, and a third energy, emitted simultaneously or with a time delay or a combination thereof. In some embodiments, energy may be a first energy, a second energy, a third energy, and an nth energy, emitted simultaneously or with a time delay or a combination thereof. Any of the a first energy, a second energy, a third energy, and a nth may be generated by at least one of a laser, an intense pulsed light, a light emitting diode, a radiofrequency generator, an acoustic source, photon-based energy source, plasma source, a magnetic resonance source, and/or a mechanical energy source.

Step 20 is accelerating healing at site. Optionally, between steps 16 and 20 is step 30, which is determining results. Between steps 16 and 30 is option step 28, which is imaging the site. The images of the site from step 28 can be useful for the determining results of step 30. If the results of step 30 are acceptable within the parameters of the treatment then Yes direction 34 is followed to step 20. If the results of step 30 are not acceptable within the parameters of the treatment then No direction 32 is followed back to step 12. After step 16, optionally traditional ultrasound heating can be applied to the site in step 27. This application of traditional ultrasound heating to the site can be useful in keeping a medicant active or providing heat to support blood perfusion to the site after step 16. Further examples and variations of treatment method 100 are discussed herein.

In addition, various different subcutaneous tissues, including for example, site, may be treated by method 100 to produce different biological effects, according to some embodiments of the present disclosure. In order to treat a specific site and to achieve a desired biological effect, ultrasound energy may be directed to a specific depth within site to reach the targeted subcutaneous tissue, such as, for example, site. For example, if it is desired to cut muscle by applying ultrasound energy 120 at ablative levels, which may be approximately 15 mm below skin surface or at other depths as described herein. An example of ablating implant and/or native tissue at site can include a series of lesions ablated into site. Besides ablating site, other biological effects may comprise incapacitating, partially incapacitating, severing, rejuvenating, removing, ablating, micro-ablating, shortening, manipulating, or removing tissue either instantly or over time, and combinations thereof.

Depending at least in part upon the desired biological effect, the implant, and the tissue being treated at site, method 100 may be used with an extracorporeal, non-invasive procedure. Also, depending at least in part upon the specific biological effect and tissue targeted, temperature may increase within site may range from approximately 30° C. to about 60° C. Other bio-effects to target tissue, such as, muscle and connective tissue layer, can include heating, cavitation, steaming, or vibro-accoustic stimulation, and combinations thereof. In various embodiments, ultrasound energy is deposited in a matrices of micro-coagulative zones to an already injured tendon or muscle can increase the "wound healing" response through the liberation of cytokines and may produce reactive changes within the native tissue at site and/or proximate to site, helping to limit surrounding tissue edema and decrease the inflammatory response at site of implant. In various embodiments, ultrasound energy deposited at site can stimulate a change to at least one of concentration and activity of inflammatory mediators (such as but not limited to TNF-A, IL-1) as well as growth factors (such as but not limited to TGF-B1, TGF-B3) at the site of the injure tendon or muscle.

In various embodiments, ultrasound energy is deposited at site, which can stimulate a change in at least one of concentration and activity of one or more of the following: Adrenomedullin (AM), Autocrine motility factor, Bone morphogenetic proteins (BMPs), Brain-derived neurotrophic factor (BDNF), Epidermal growth factor (EGF), Erythropoietin (EPO), Fibroblast growth factor (FGF), Glial cell line-derived neurotrophic factor (GDNF), Granulocyte colony-stimulating factor (G-CSF), Granulocyte macrophage colony stimulating factor (GM-CSF), Growth differentiation factor-9 (GDF9), Hepatocyte growth factor (HGF), Hepatoma-derived growth factor (HDGF), Insulin-like growth factor (IGF), Migration-stimulating factor, Myostatin (GDF-8), Nerve growth factor (NGF) and other neurotrophies, Platelet-derived growth factor (PDGF), Thrombopoietin (TPO), Transforming growth factor alpha (TGF-a), Transforming growth factor beta(TGF-β), Tumor necrosis factor-alpha(TNF-α), Vascular endothelial growth factor (VEGF), Wnt Signaling Pathway, placental growth factor (PIGF), [(Foetal Bovine Somatotrophin)] (FBS), IL-1-Cofactor for IL-3 and IL-6, which can activate T cells, IL-2-T-cell growth factor, which can stimulate IL-1 synthesis and can activate B-cells and NK cells, IL-3, which can stimulate production of all non-lymphoid cells, IL-4-Growth factor for activating B cells, resting T cells, and mast cells, IL-5, which can induce differentiation of activated B cells and eosinophils, IL-6, which can stimulate Ig synthesis and growth factor for plasma cells, IL-7 growth factor for pre-B cells, and/or any other growth factor not listed herein, and combinations thereof.

Further, medicants, as described above, can include a drug, a medicine, or a protein, and combinations thereof. Medicants can also include adsorbent chemicals, such as zeolites, and other hemostatic agents are used in sealing severe injuries quickly. Thrombin and fibrin glue are used surgically to treat bleeding and to thrombose aneurysms. Medicants can include Desmopressin is used to improve platelet function by activating arginine vasopressin receptor 1A. Medicants can include coagulation factor concentrates are used to treat hemophilia, to reverse the effects of anticoagulants, and to treat bleeding in patients with impaired coagulation factor synthesis or increased consumption. Prothrombin complex concentrate, cryoprecipitate and fresh frozen plasma are commonly-used coagulation factor products. Recombinant activated human factor VII can be used in the treatment of major bleeding. Medicants can include tranexamic acid and aminocaproic acid, can inhibit fibrinolysis, and lead to a de facto reduced bleeding rate. In addition, medieants can include steroids like the glucocorticoid cortisol.

According to various embodiments of method 100, ultrasound probe is coupled directly to site, as opposed to skin surface, to treat targeted tissue and/or implant. For example, ultrasound probe can be integrated to or attached to a tool, such as, for example, an arthroscopic tool, laparoscopic tool, or an endoscopic tool that may be inserted into a patient's body with minimal invasiveness.

In some embodiments, cosmetic enhancement can refer to procedures, which are not medically necessary and are used to improve or change the appearance of a portion of the body. For example, a cosmetic enhancement can be a procedure but not limited to procedures that are used to improve or change the appearance of a nose, eyes, eyebrows and/or other facial features, or to improve or change the appearance and/or the texture and/or the elasticity of skin, or to improve or change the appearance of a mark or scar on a skin surface. According to various embodiments, method 100 results in cosmetic enhancement of a portion of the body. For example, an implant can be silicone or saline breast implants for the cosmetic enhancement of breasts. In another example, an implant can be a cheek implant for the cosmetic enhancement of a face. An implant can be a cosmetic filler, which may be injected below a skin surface.

Figure 2:
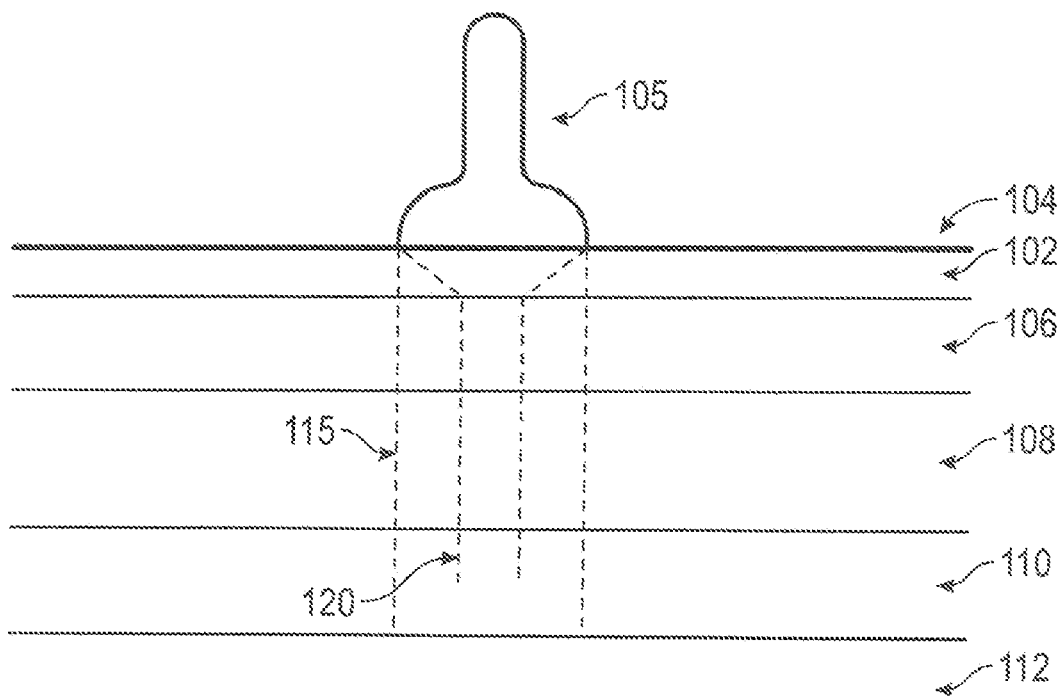
FIG. 2 is a cross sectional view illustrating ultrasound energy directed to layers of subcutaneous tissue, according to various non-limiting embodiments.

Now moving to FIG. 2, a cross sectional view of tissue layers and ultrasound energy directed to layers of subcutaneous tissue, according to various embodiments, is illustrated. Typically, ultrasound energy propagates as a wave with relatively little scattering, over depths up to many centimeters in tissue depending on the ultrasound frequency. The focal spot size achievable with any propagating wave energy depends on wavelength. Ultrasound wavelength is equal to the acoustic velocity divided by the ultrasound frequency. Attenuation (absorption, mainly) of ultrasound by tissue also depends on frequency. Shaped lesion can be created through adjustment of the strength, depth, and type of focusing, energy levels and timing cadence. For example, focused ultrasound can be used to create precise arrays of microscopic thermal ablation zones. Ultrasound energy 120 can produce an array of ablation zones deep into the layers of the soft tissue. Detection of changes in the reflection of ultrasound energy can be used for feedback control to detect a desired effect on the tissue and used to control the exposure intensity, time, and/or position.

In various embodiment, ultrasound probe 105 is configured with the ability to controllably produce conformal lesions of thermal injury in soft tissue within ROI 115 through precise spatial and temporal control of acoustic energy deposition, i.e., control of ultrasound probe 105 is confined within selected time and space parameters, with such control being independent of the tissue. The ultrasound energy 120 can be controlled using spatial parameters. The ultrasound energy 120 can be controlled using temporal parameters. The ultrasound energy 120 can be controlled using a combination of temporal parameters and spatial parameters.

In accordance with various embodiments, control system and ultrasound probe 105 can be configured for spatial control of ultrasound energy 120 by controlling the manner of distribution of the ultrasound energy 120. For example, spatial control may be realized through selection of the type of one or more transducer configurations insonifying ROI 115, selection of the placement and location of ultrasound probe 105 for delivery of ultrasound energy 120 relative to ROI 115 e.g., ultrasound probe 105 being configured for scanning over part or whole of ROI 115 to produce contiguous thermal injury having a particular orientation or otherwise change in distance from ROI 115, and/or control of other environment parameters, e.g., the temperature at the acoustic coupling interface can be controlled, and/or the coupling of ultrasound probe 105 to tissue. Other spatial control can include but are not limited to geometry configuration of ultrasound probe 105 or transducer assembly, lens, variable focusing devices, variable focusing lens, stand-offs movement of ultrasound probe, in any of six degrees of motion, transducer backing, matching layers, number of transduction elements in transducer, number of electrodes, or combinations thereof.

In various embodiments, control system and ultrasound probe 105 can also be configured for temporal control, such as through adjustment and optimization of drive amplitude levels, frequency, waveform selections, e.g., the types of pulses, bursts or continuous waveforms, and timing sequences and other energy drive characteristics to control thermal ablation of tissue. Other temporal control can include but are not limited to full power burst of energy, shape of burst, timing of energy bursts, such as, pulse rate duration, continuous, delays, etc., change of frequency of burst, burst amplitude, phase, apodization, energy level, or combinations thereof.

The spatial and/or temporal control can also be facilitated through open-loop and closed-loop feedback arrangements, such as through the monitoring of various spatial and temporal characteristics. As a result, control of acoustical energy within six degrees of freedom, e.g., spatially within the X, Y and Z domain, as well as the axis of rotation within the XY, YZ and XZ domains, can be suitably achieved to generate conformal lesions of variable shape, size and orientation. For example, through such spatial and/or temporal control, ultrasound probe 105 can enable the regions of thermal injury to possess arbitrary shape and size and allow the tissue to be destroyed (ablated) in a controlled manner.

The tissue layers illustrated are skin surface 104, epidermal layer 102, dermis layer 106, fat layer 108, SMAS layer 110, and muscle and connective tissue layer 112. Ultrasound probe 105 emits ultrasound energy 120 in ROI 115. In various embodiments, ultrasound probe 105 is capable of emitting ultrasound energy 120 at variable depths in ROI 115, such as, for example, the depths described herein. Ultrasound probe 105 is capable of emitting ultrasound energy as a single frequency, variable frequencies, or a plurality of frequencies, such as, for example, the frequency ranges described herein. Ultrasound probe 105 is capable of emitting ultrasound energy 120 for variable time periods or to pulse the emission over time, such as, for example, those time intervals described herein. Ultrasound probe 105 is capable of providing various energy levels of ultrasound energy, such as, for example, the energy levels described herein. Ultrasound probe 105 may be individual hand-held device, or may be part of a treatment system. The ultrasound probe 105 can provide both ultrasound energy and imaging ultrasound energy. However, ultrasound probe 105 may provide only ultrasound energy. Ultrasound probe 105 may comprise a therapeutic transducer and a separate imaging transducer. Ultrasound probe 105 may comprise a transducer or a transducer array capable of both therapeutic and imaging applications. According an alternative embodiment, ultrasound probe 105 is coupled directly to one of the tissue layers, as opposed to skin surface 104 to treat the tissue layer. For example, ultrasound probe can be integrated to or attached to a tool, such as, for example, an arthroscopic tool, laparoscopic tool, or an endoscopic tool that may be inserted into a patient's body with minimal invasiveness.

In various embodiments, ultrasound probe 105 may be used for method 100. In various embodiments, method 100 can be implemented using any or all of the elements illustrated in FIG. 2. As will be appreciated by those skilled in the art, at least a portion of method 100 or a variation of method 100 can be implemented using any or all of the elements illustrated in FIG. 2.

In some embodiments, ultrasound energy 120 ablates a portion of a tissue layer and/or site creating a lesion. In some embodiments, ultrasound energy 120 ablates a portion of implant and/or native tissue creating a lesion. In some embodiments ultrasound energy coagulates a portion of implant and/or native tissue. In some embodiments ultrasound energy 120 coagulates a portion site.

In some embodiments, ultrasound probe 105 can be moved in at least one direction to provide a plurality of lesions in a tissue layer or at site, in various embodiments, a plurality of lesions can be placed in a pattern in at least one tissue layer, such as, for example, a 1-D pattern, a 2-D pattern, a 3-D pattern, or combinations thereof. In some embodiments, ultrasound probe 105 comprises a single transducer element and while emitting ultrasound energy 120 in a pulsed matter, is moved in a linear motion along skin surface 104 to create a 1-D pattern of a plurality of lesions in at least one tissue layer. In some embodiments, ultrasound probe 105 comprises a linear array of transducers and while emitting ultrasound energy 120 in a pulsed matter, is moved along the linear vector of the array on skin surface 104 to create a 1-D pattern of a plurality of lesions in at least one tissue layer.

In some embodiments, ultrasound probe 105 comprises a linear array of transducers and while emitting ultrasound energy 120 in a pulsed matter, is moved along the non-linear vector of the array on skin surface 104 to create a 2-D pattern of a plurality of lesions in at least one tissue layer. In some embodiments, ultrasound probe 105 comprises an array of transducers and while emitting ultrasound energy 120 in a pulsed matter, is moved along skin surface 104 to create a 2-D pattern of a plurality of lesions in at least one tissue layer.

In some embodiments, ultrasound probe 105 comprises an array of transducers, wherein the array comprises a first portion focusing to a first depth and a second portion focusing to a second depth, and while emitting ultrasound energy 120 in a pulsed matter, is moved along skin surface 104 to create a 3-D pattern of a plurality of lesions in at least one tissue layer. In some embodiments, ultrasound probe 105 comprises at least two arrays of transducers, wherein a first array focusing to a first depth and a second array focusing to a second depth, and while each of the arrays emitting ultrasound energy 120 in a pulsed matter, is moved along skin surface 104 to create a 3-D pattern of a plurality of lesions in at least one tissue layer. In some embodiments, ultrasound probe 105 comprises a linear array of transducers and while emitting ultrasound energy 120 in a pulsed matter, is moved along the non-linear vector of the array on skin surface 104 focused to a first depth then moved in the same direction along skin surface focused at a second depth to create a 3-D pattern of a plurality of lesions in at least one tissue layer. In some embodiments, ultrasound probe 105 comprises an array of transducers and while emitting ultrasound energy 120 in a pulsed matter, is moved along skin surface 104 focused to a first depth then moved in the same direction along skin surface focused at a second depth to create a 3-D pattern of a plurality of lesions in at least one tissue layer.

In various embodiments, methods, described herein, can stimulate coagulation by depositing target ultrasound energy with or without a medicant. Coagulation is a complex process by which blood forms clots. It is an important part of hemostasis (the cessation of blood loss from a damaged vessel), wherein a damaged blood vessel wall is covered by a platelet and fibrin-containing clot to stop bleeding and begin repair of the damaged vessel. Disorders of coagulation can lead to an increased risk of bleeding (hemorrhage) or obstructive clotting (thrombosis).

Coagulation begins almost instantly after an injury to the blood vessel has damaged the endothelium (lining of the vessel). Exposure of the blood to proteins such as tissue factor initiates changes to blood platelets and the plasma protein fibrinogen, a clotting factor. Platelets immediately form a plug at the site of injury; this is called primary hemostasis. Secondary hemostasis occurs simultaneously: Proteins in the blood plasma, called coagulation factors or clotting factors, respond in a complex cascade to form fibrin strands, which strengthen the platelet plug.

In some embodiments, methods, described herein, can initiate coagulation cascade by depositing target ultrasound energy with or without a medicant. The coagulation cascade of secondary hemostasis has two pathways which lead to fibrin formation. These are the contact activation pathway (formerly known as the intrinsic pathway), and the tissue factor pathway (formerly known as the extrinsic pathway). It was previously thought that the coagulation cascade consisted of two pathways of equal importance joined to a common pathway. It is now known that the primary pathway for the initiation of blood coagulation is the tissue factor pathway. The pathways are a series of reactions, in which a zymogen (inactive enzyme precursor) of a serine protease and its glycoprotein co-factor are activated to become active components that then catalyze the next reaction in the cascade, ultimately resulting in cross-linked fibrin.

The coagulation factors are generally serine proteases (enzymes). There are some exceptions. For example, FVIII and FV are glycoproteins, and Factor XIII is a transglutaminase. Serine proteases act by cleaving other proteins at specific sites. The coagulation factors circulate as inactive zymogens. The coagulation cascade is classically divided into three pathways. The tissue factor and contact activation pathways both activate the "final common pathway" of factor X, thrombin and fibrin.

Soon after implantation of implant and/or artificial skin, a wound healing cascade is unleashed. This cascade is usually said to take place in three phases: the inflammatory, proliferative, and maturation stages.

In some embodiments, methods, described herein, can peak inflammation by depositing target ultrasound energy with or without a medicant. In the inflammatory phase, macrophages and other phagocytic cells kill bacteria, debride damaged tissue and release chemical factors such as growth hormones that encourage fibroblasts, epithelial cells and endothelial cells which make new capillaries to migrate to the area and divide.

In the proliferative phase, immature granulation tissue containing plump active fibroblasts forms. Fibroblasts quickly produce abundant type III collagen, which fills the defect left by an open wound. Granulation tissue moves, as a wave, from the border of the injury towards the center.

As granulation tissue matures, the fibroblasts produce less collagen and become more spindly in appearance. They begin to produce the much stronger type I collagen. Some of the fibroblasts mature into myofibroblasts which contain the same type of actin found in smooth muscle, which enables them to contract and reduce the size of the wound.

During the maturation phase of wound healing, unnecessary vessels formed in granulation tissue are removed by apoptosis, and type III collagen is largely replaced by type I. Collagen which was originally disorganized is cross-linked and aligned along tension lines. This phase can last a year or longer. Ultimately a scar made of collagen, containing a small number of fibroblasts is left.

In one outcome of inflammation and healing, fibrosis can occur. Large amounts of tissue destruction, or damage in tissues unable to regenerate cannot be regenerated completely by the body. Fibrous scarring occurs in these areas of damage, forming a scar composed primarily of collagen. The sear will not contain any specialized structures, such as parenchymal cells, hence functional impairment may occur.

According to various embodiments, methods can include non-invasive shrinkage or removal of a fibrous scar located in site. Such a method can include targeting the fibrous scar in ROI 115, directing ablative ultrasound energy to the fibrous sear, ablating at least a portion of the fibrous scar, and shrinking or removing the fibrous scar. The method can also include imaging the fibrous scar. The method can also include imaging the scar after the ablating at least a portion of the fibrous scar. The method can include comparing a measurement of the scar before and after the ablating step. The method can include directing acoustical pressure or cavitation to the scar after the ablating step to further break up the scar. The method can include increasing blood perfusion to the ROI 115. The method can also include any of the steps of method 100.

In another outcome of inflammation and healing, an abscess can be formed. A cavity is formed containing pus, which is a liquid comprising dead white blood cell, and bacteria mixed with destroyed cells. According to various embodiments, methods can include non-invasive removal of an abscess located in site. Such a method can include targeting the abscess in ROI 115, directing ablative ultrasound energy to the abscess, ablating at least a portion of the abscess, and shrinking or removing the abscess. The method can also include imaging the abscess. The method can also include imaging the abscess after the ablating at least a portion of the abscess. The method can include comparing a measurement of the abscess before and after the ablating step. The method can include directing acoustical pressure or cavitation to the scar after the ablating step to further break up the abscess. The method can include destroying bacteria located in the abscess. The method can include increasing blood perfusion to the ROI 115. The method can include administering a medicant to the ROI 115. The method can also include any of the steps of method 100.

Figure 3A:
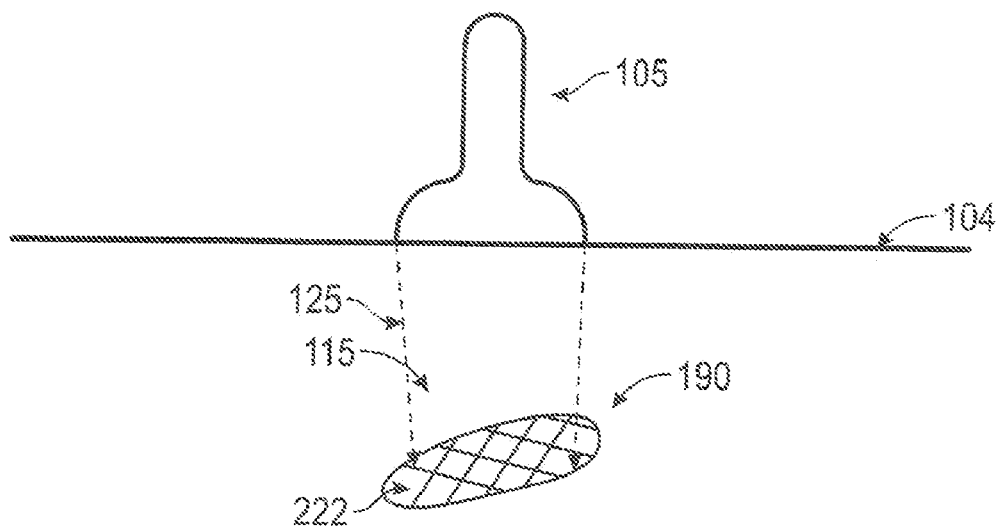
FIG. 3A illustrates various steps of a method, according to various non-limiting embodiments.
Figure 3B:
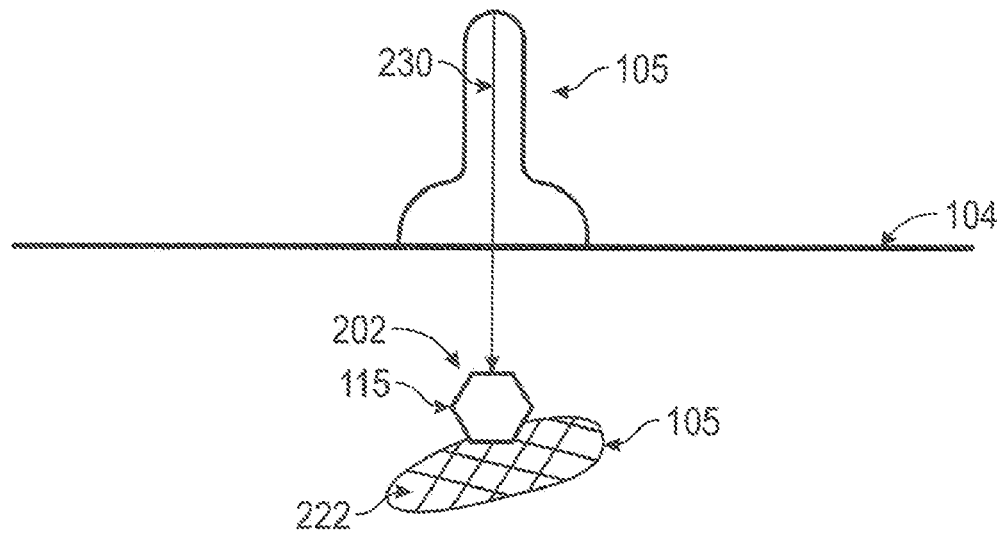
FIG. 3B illustrates various steps of a method, accordingly to various non-limiting embodiments.
Figure 3C:
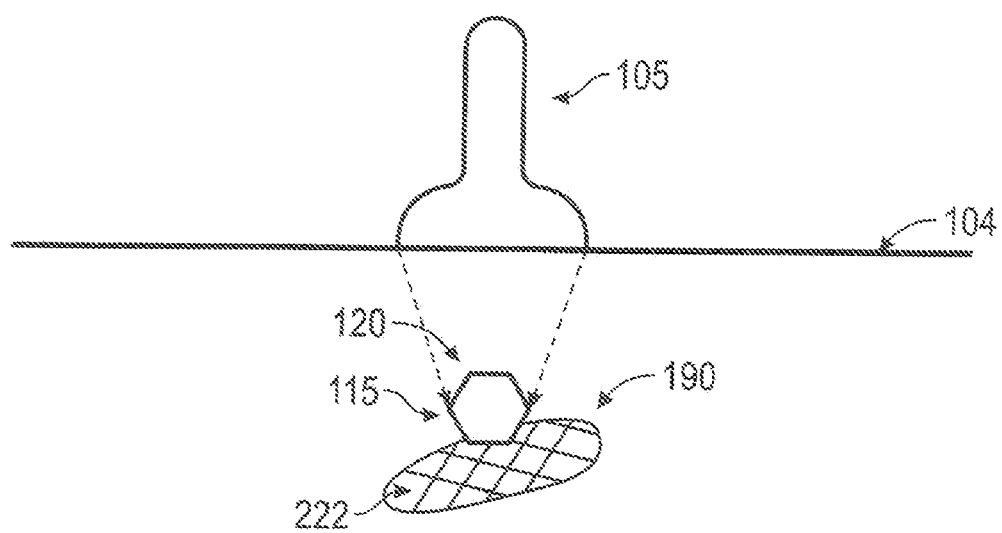
FIG. 3C illustrates various steps of a method, accordingly to various non-limiting embodiments.
Figure 4A:
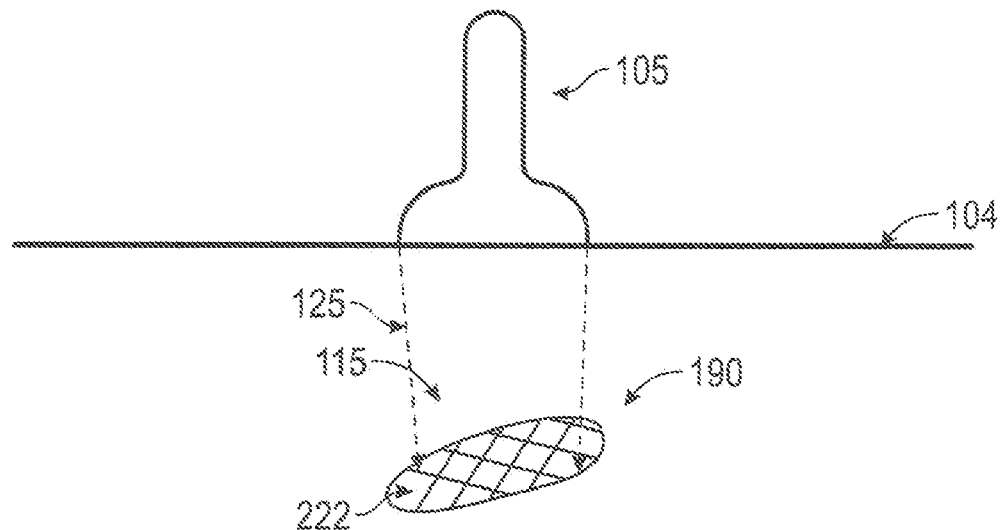
FIG. 4A illustrates various steps of a method, according to various non-limiting embodiments.
Figure 4B:
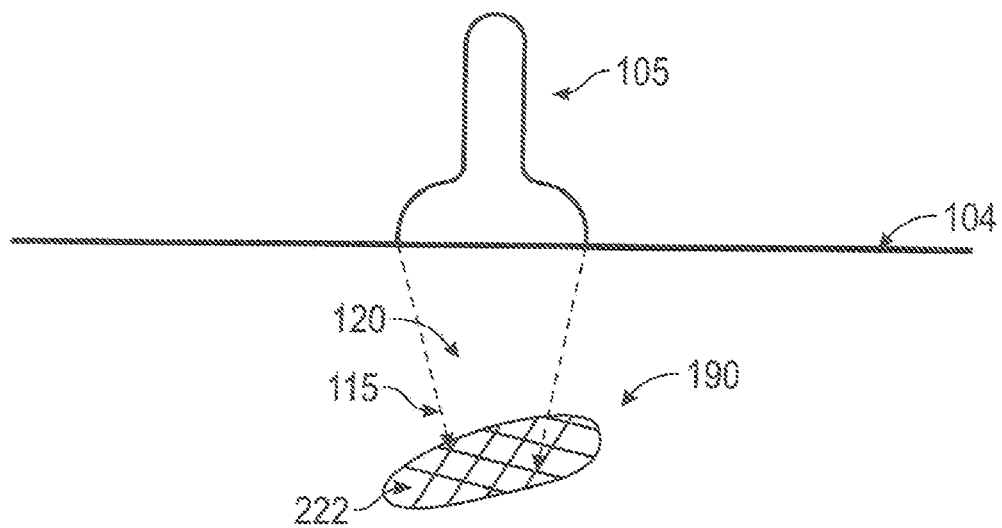
FIG. 4B illustrates various steps of a method, according to various non-limiting embodiments.
Figure 4C:
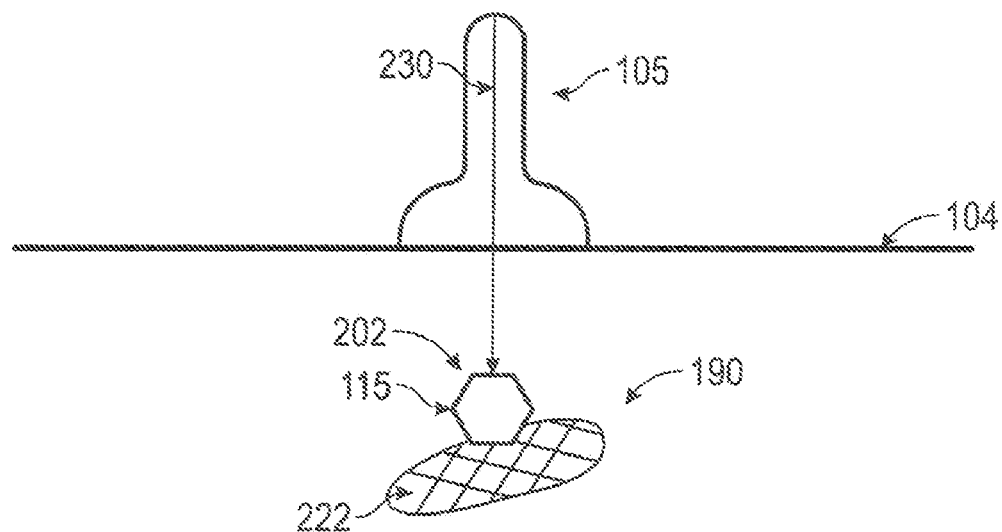
FIG. 4C illustrates various steps of a method, according to various non-limiting embodiments.
Figure 4D:
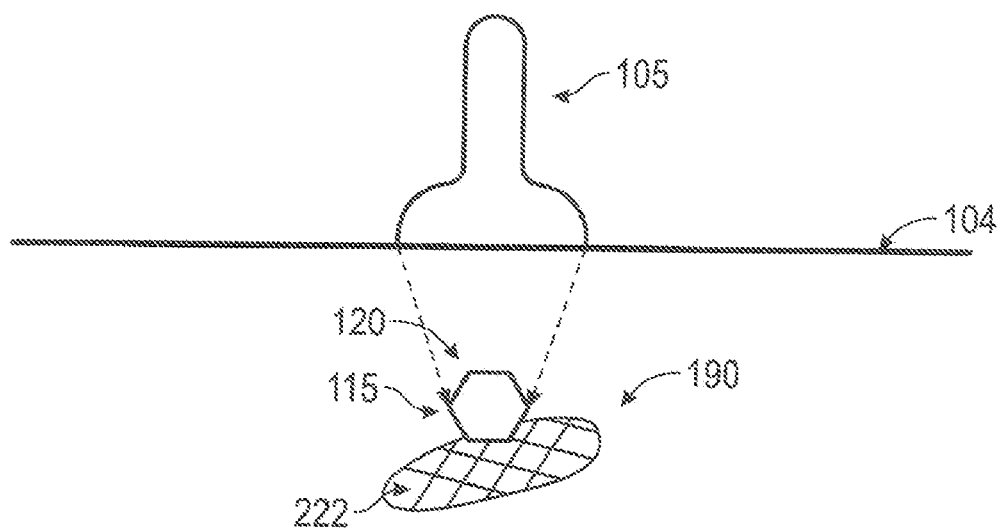
FIG. 4D illustrates various steps of a method, according to various non-limiting embodiments.

With reference to FIGS. 3A-C, method and apparatus for accelerating integration of implant into a site are illustrated. According to various embodiments, implant 222 can be placed at site 190 below surface 104. ROI 115 includes at least a portion of implant 222. Probe 105 can be coupled to surface 104 and imaging ultrasound energy 125 can be directed to ROI 115. Site 190 can be imaged. Implant 222 can be imaged. In some embodiments, implant 222 and site 190 can be mapped using imaging ultrasound energy 125. An image of at least one of implant 222 and site 190 can be displayed. According to various embodiments, imaging of at least one of implant 222 and site 190 can be used to identify a target for directing medicant 202.

In accordance to various embodiments, implant 222 can be a medical device manufactured to replace missing biological structure, support damage biological structure, or enhance existing biological structure. For example, implant 222 can be a mesh, scaffold, a screw, a bone graph, a pin, a plate, a rod, a stent, and combinations thereof. Implant 222 can be a joint replacement or any portion thereof. Implant 222 can be made of a metal, such as titanium, molybdenum, stainless steel, and combinations thereof. Implant 222 can be biosorbable. Implant 222 can be a dental implant. Implant 222 can be a prosthetic. In some embodiments, implant may comprise a biomaterial. In some embodiments, implant 222 can be a breast implant or other silicone or saline encased implant. In some embodiments, implant 222 can be a bone graph. In some embodiments, implant 22 is artificial skin. As described herein, implant 222 can be any device, material, biomaterial, or combinations thereof that are known to those skilled in the art as an implant or are created in the future.

In various embodiments, site 190 can include native tissue. For example, site 190 can comprise implant 222 and native tissue of patient. In some embodiments, native tissue can comprise, for example, soft tissue, subcutaneous tissue, muscle, bone, skin, tendon, ligament, cartilage, a vein, an artery, a blood vessel, a portion of a heart, a portion of a spine, at least portion of a joint, a tooth, a portion of tissue of the face or neck, and combinations thereof.

Medicant 202 can be any chemical or naturally occurring substance that has an active component. For example a medicant 202 can be, but not limited to, a pharmaceutical, a drug, a medication, a vaccine, an antibody, a nutriceutical, an herb, a vitamin, a cosmetic, an amino acid, a protein, a sugar, a recombinant material, a collagen derivative, blood, blood components, somatic cell, gene therapy, tissue, recombinant therapeutic protein, stem cells, a holistic mixture, and combinations thereof. Medicant 202 can also include a biologic, such as for example a recombinant DNA therapy, synthetic growth hormone, monoclonal antibodies, or receptor constructs.

Medicant 202 can be administered by applying it to the skin above the ROI. Medicant 202 can be driven into subcutaneous tissue below the skin by ultrasound energy. The ultrasound energy may be provide mechanical motion, such as, vibrational, cavitation, harmonics, and/or pressure gradients, or provide a thermal gradient. A medicant 202 can be mixed in a coupling gel or can be used as a coupling gel. The medicant 202 can be administered to the circulatory system. For example, the medicant 202 can be in the blood stream and can be activated or moved to the ROI by the ultrasound energy. Medicant 202 can be administered by injection into or near the ROI. The medicant 202 can be activated by ultrasound energy.

Any naturally occurring proteins, stem cells, growth factors and the like can be used as medicant 202 in accordance to various embodiments. A medicant 202 can also include adsorbent chemicals, such as zeolites, and other hemostatic agents are used in sealing severe injuries quickly. Medicant 202 can be thrombin and/or fibrin glue which can be used surgically to treat bleeding and to thrombose aneurysms. Medicant 202 can include Desmopressin, which can be used to improve platelet function by activating arginine vasopressin receptor 1A. Medicant 202 can include coagulation factor concentrates, which can be used to treat hemophilia, to reverse the effects of anticoagulants, and to treat bleeding in patients with impaired coagulation factor synthesis or increased consumption. Prothrombin complex concentrate, cryoprecipitate and fresh frozen plasma are commonly-used coagulation factor products. Recombinant activated human factor VII can be used in the treatment of major bleeding. Medicant 202 can include tranexamic acid and aminocaproic acid, which can inhibit fibrinolysis, and lead to a de facto reduced bleeding rate. In addition, medicant 202 can include steroids, (anabolic steroids and/or cortisol steroids), for example glucocorticoid cortisol or prednisone. Medicant 202 can include compounds as alpha lipoic acid, DMAE, vitamin C ester, tocotrienols, and phospholipids.

Medicant 202 can be a pharmaceutical compound such as for example, cortisone, Etanercept, Ahatacept, Adalimumab, or infliximab. Medicant 202 can include platelet-rich plasma (PRP), mesenchymal stem cells, or growth factors. For example, PRP is typically a fraction of blood that has been centrifuged. The PRP is then used for stimulating healing of the injury. The PRP typically contains thrombocytes (platelets) and cytokines (growth factors). The PRP may also contain thrombin and may contain fibenogen, which when combined can form fibrin glue. Medicant 202 can be a prothrombin complex concentrate, cryoprecipitate and fresh frozen plasma, which are commonly-used coagulation factor products. Medicant 202 can be a recombinant activated human factor VII, which can be used in the treatment of major bleeding. Medicant 202 can include tranexamic acid and aminocaproic acid, can inhibit fibrinolysis, and lead to a de facto reduced bleeding rate.

Referring back to FIGS. 3 A-C, needle 230 can be inserted through surface 104 and employed to direct medicant 202 to at least one of site 190 and implant 222. In other embodiments, ultrasound energy can create a pressure gradient to direct medicant 202 through surface 104 at least one of site 190 and implant 222. In various embodiments, ultrasound energy 120 is directed to at least one of site 190 and implant 222. In some embodiments, ultrasound energy 120 can ablate a portion of site 190. In some embodiments, ultrasound energy 120 can be focused to a portion of site 190. In some embodiments, ultrasound imaging 120 can create a lesion in a portion of site 190. In some embodiments, ultrasound energy can coagulate a portion of site 190. In some embodiments, ultrasound energy 120 can weld implant 222 portion of site 190. In some embodiments, ultrasound energy 120 increases blood perfusion to site 190. In some embodiments, ultrasound energy accelerates inflammation peaking which may stimulate healing at site 190. In some embodiments, ultrasound energy 120 activates medicant 202. In some embodiments, medicant 202 is coated on at least a portion of implant 222. In such embodiments, ultrasound energy activates medicant 202 that is coated on implant 222.

With reference to FIGS. 4A-D, method and apparatus for accelerating integration of implant into a site are illustrated. According to various embodiments, implant 222 can be placed at site 190 below surface 104. ROI 115 includes at least a portion of implant 222. Probe 105 can be coupled to surface 104 and imaging ultrasound energy 125 can be directed to ROI 115. Site 190 can be imaged. Implant 222 can be imaged. In some embodiments, implant 222 and site 190 can be mapped using imaging ultrasound energy 125. An image of at least one of implant 222 and site 190 can be displayed. According to various embodiments, imaging of at least one of implant 222 and site 190 can be used to identify a target for directing medicant 202.

In various embodiments, ultrasound energy 120 is directed to at least one of site 190 and implant 222. In some embodiments, ultrasound energy 120 can ablate a portion of site 190. In some embodiments, ultrasound energy 120 can be focused to a portion of site 190. In some embodiments, ultrasound imaging 120 can create a lesion in a portion of site 190. In some embodiments, ultrasound energy can coagulate a portion of site 190.

According to various embodiments, needle 230 can be inserted through surface 104 and employed to direct medicant 202 to at least one of site 190 and implant 222. In other embodiments, ultrasound energy can create a pressure gradient to direct medicant 202 through surface 104 at least one of site 190 and implant 222. In various embodiments, ultrasound energy 120 is directed to at least one of site 190 and implant 222. In some embodiments, ultrasound energy 120 can ablate a portion of site 190. In some embodiments, ultrasound energy 120 can be focused to a portion of site 190. In some embodiments, ultrasound energy 120 can weld implant 222 portion of site 190. In some embodiments, ultrasound energy 120 increases blood perfusion to site 190. In some embodiments, ultrasound energy accelerates inflammation peaking which may stimulate healing at site 190. In some embodiments, ultrasound energy 120 activates medicant 202. In some embodiments, medicant 202 is coated on at least a portion of implant 222. In such embodiments, ultrasound energy activates medicant 202 that is coated on implant 222.

According to various embodiments, a method can include targeting micro-tears within site 190, directing ultrasound energy 120 to the micro-tears within site 190, ablating at least a portion of the micro-tears, and improving the micro-tears within site 190. In some embodiments, the method further includes placing or directing a medicant into an area that includes at least a portion of the micro-tears within site 190. The directing ultrasound energy 120 to the micro-tears within site 190 can be before, during and/or after the placing or directing a medicant into an area that includes at least a portion of the micro-tears within site 190.

Figure 5:
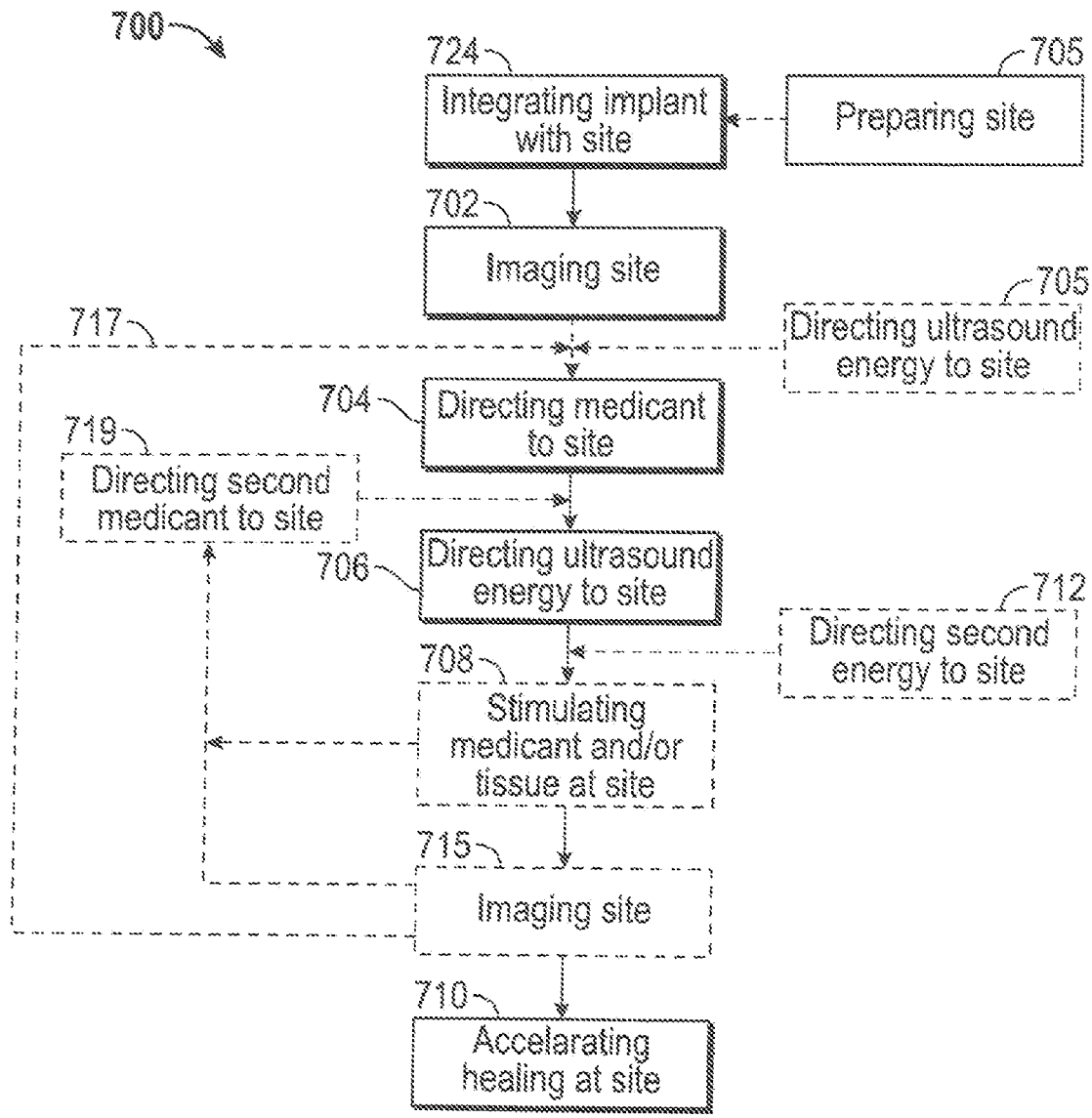
FIG. 5 is a flow chart illustrating method, according to various non-limiting embodiments.

Now referring to FIG. 5, a method of integrating implant to site this illustrated. In various embodiments, a method can include imaging implant 702 and/or native tissue at site. In various embodiments, site can include native tissue, as described herein. For example, site can comprise implant and native tissue of patient. The various embodiments, a method can include placing or directing a medicant 704 to at least one of implant and/or native tissue at site. In some embodiments, a method can include directing ultrasound energy 705 to the site after the step of imaging implant 702. In various embodiments, a method can include directing ultrasound energy 706 to at least one of implant, medicant, and native tissue at site. In various embodiments, a method can include stimulating or activating 708 at least one of medicant and native tissue. In various embodiments of method can include accelerating integration 710 of implant to native tissue at site. In some embodiments, a method can include imaging site 715 after stimulating or activating 708 at least one of implant, medicant and native tissue. In some embodiments, the method can include placing a second medicant at site 719 then directing ultrasound energy 706 to at least one of implant, second medicant, and native tissue. In some embodiments, after imaging site 715 decision 117 to loop back and repeat certain steps of method as described herein. In some embodiments the method can include preparing implant site 722 and/or integrating implant into site 724 before the step of imaging implant 702. As will be apparent to those skilled in the art, hashed lines and hashed boxes indicate steps which are optional in method 700.

In various embodiments of method can include accelerating integration 710 of implant to native tissue at site, which can be a biological effect. A biological effect can be stimulating or increase an amount of heat shock proteins. Such a biological effect can cause white blood cells to promote healing of a portion of native tissue at site. A biological effect can be to restart or increase the wound healing cascade at the site. A biological effect can be increasing the blood perfusion to the site. A biological effect can be encouraging collagen growth. A biological effect may increase the liberation of cytokines and may produce reactive changes within the subcutaneous layer. A biological effect may by peaking inflammation at site. A biological effect may be the disruption or modification of biochemical cascades. A biological effect may be the production of new collagen. A biological effect may be a stimulation of cell growth at site. A biological effect may be angiogenesis. A biological effect may be stimulation or activation of coagulation factors. A biological effect may a cell permeability response. A biological effect may be an enhanced delivery of medicants to soft tissue, such as for example, native tissue.

In various embodiments, methods can provide a controlled release of a medicant, which to assist and/or accelerate adoption of implant to native tissue.

In various embodiments, ultrasound energy changes at least one of concentration and activity of inflammatory mediators (TNF-A, IL-1) as well as growth factors (TGF-B1, TGE-B3) at site. In various embodiments, ultrasound energy accelerates inflammation peaking, which can accelerate various healing cascades.

In various embodiments, method 700 can include accelerating healing at site 710, which can include stimulating a change in at least one of concentration and activity of one or more of the following: Adrenomedullin (AM), Autocrine motility factor, Bone morphogenetic proteins (BMPs), Brain-derived neurotrophic factor (BDNF), Epidermal growth factor (EGF), Erythropoietin (EPO), Fibroblast growth factor (FGF), Glial cell line-derived neurotrophic factor (GDNF), Granulocyte colony-stimulating factor (G-CSF), Granulocyte macrophage colony-stimulating factor (GM-CSF), Growth differentiation factor-9 (GDF9), Hepatocyte growth factor (IMF), Hepatoma-derived growth factor (HDGF). Insulin-like growth factor (IGF), Migration-stimulating factor, Myostatin (GDF-8), Nerve growth factor (NGF) and other neurotrophins, Platelet-derived growth factor (PDGF), Thrombopoietin (TPO), Transforming growth factor alpha(TGF-α), Transforming growth factor beta(TGF-β), Tumor necrosis factor-alpha(TNF-α), Vascular endothelial growth factor (VEGF), Wnt Signaling Pathway, placental growth factor (PIGF), [(Foetal Bovine Somatotrophin)] (FBS), IL-1-Cofactor for IL-3 and IL-6, which can activate T cells, IL-2-T-cell growth factor, which can stimulate IL-1 synthesis and can activate B-cells and NK cells, IL-3, which can stimulate production of all non-lymphoid cells, IL-4. Growth factor for activating B cells, resting T cells, and mast cells, IL-5, which can induce differentiation of activated B cells and eosinophils, IL-6, which can stimulate Ig synthesis and growth factor for plasma cells, IL-7 growth factor for pre-B cells, and/or any other growth factor not listed herein, and combinations thereof.

Figure 6A:
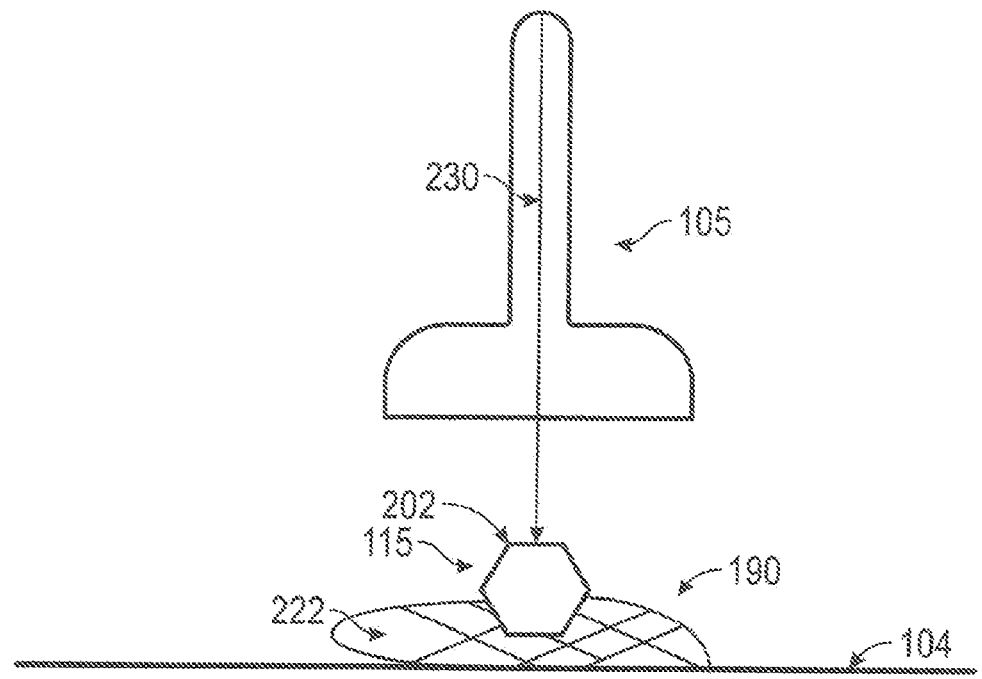
FIG. 6A illustrates various steps of a method, according to various non-limiting embodiments.
Figure 6B:
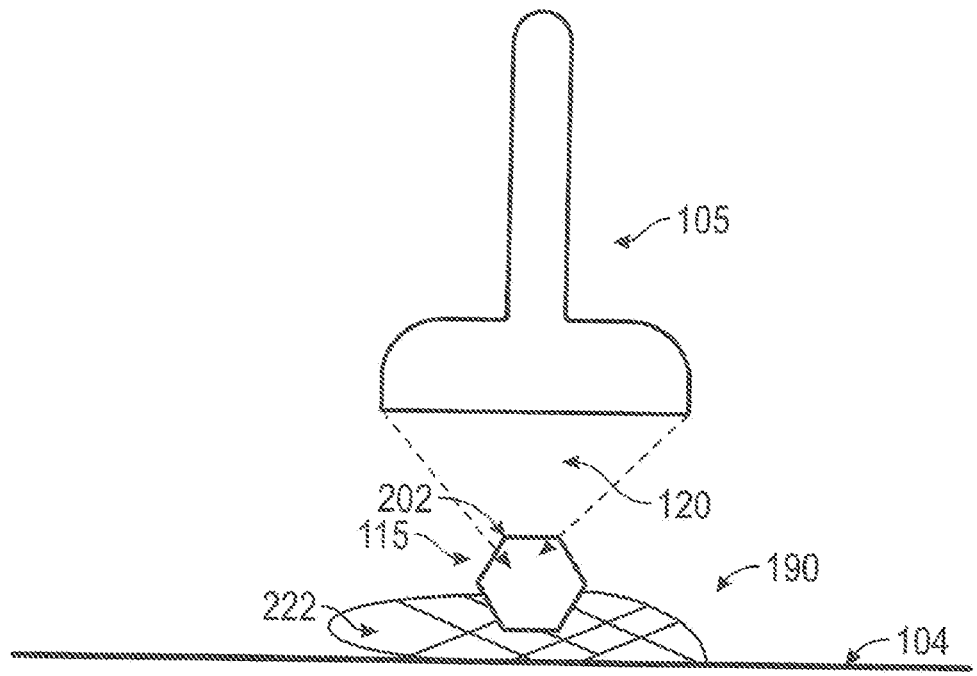
FIG. 6B illustrates various steps of a method, according to various non-limiting embodiments.

Moving on to FIG. 6A-B, method and apparatus for accelerating integration of implant onto a site are illustrated.

According to various embodiments, implant 222 can be placed at site 190 on or slightly below surface 104. ROI 115 includes at least a portion of implant 222. In some embodiments, implant 22 is artificial skin. In some embodiments, probe 105 can optionally image site 190 (not shown). In some embodiments, probe 105 comprises a stand-off. In some embodiments, probe 105 comprises a lens. In some embodiments, probe comprises automated transducer motion mechanism to move transducer into a location to direct ultrasound energy 120 to site 190 on surface 104.

According to various embodiments, needle 230 can be inserted through surface 104 and employed to direct medicant 202 to at least one of site 190 and implant 222. In other embodiments, ultrasound energy can create a pressure gradient to direct medicant 202 on surface 104 to at least one of site 190 and implant 222. In various embodiments, ultrasound energy 120 is directed to at least one of site 190 and implant 222. In some embodiments, ultrasound energy 120 can ablate a portion of site 190. In some embodiments, ultrasound energy 120 can be focused to a portion of site 190. In some embodiments, ultrasound energy 120 can weld implant 222 portion of site 190. In some embodiments, ultrasound energy 120 increases blood perfusion to site 190. In some embodiments, ultrasound energy accelerates inflammation peaking which may stimulate healing at site 190. In some embodiments, ultrasound energy 120 activates medicant 202. In some embodiments, medicant 202 is coated on at least a portion of implant 222. In such embodiments, ultrasound energy activates medicant 202 that is coated on implant 222.

According to various embodiments, a method can include targeting micro-tears within site 190, directing ultrasound energy 120 to the micro-tears within site 190, ablating at least a portion of the micro-tears, and improving the micro-tears within site 190. In some embodiments, the method further includes placing or directing a medicant into an area that includes at least a portion of the micro-tears within site 190. The directing ultrasound energy 120 to the micro-tears within site 190 can be before, during and/or after the placing or directing a medicant into an area that includes at least a portion of the micro-tears within site 190.

Figure 7A:
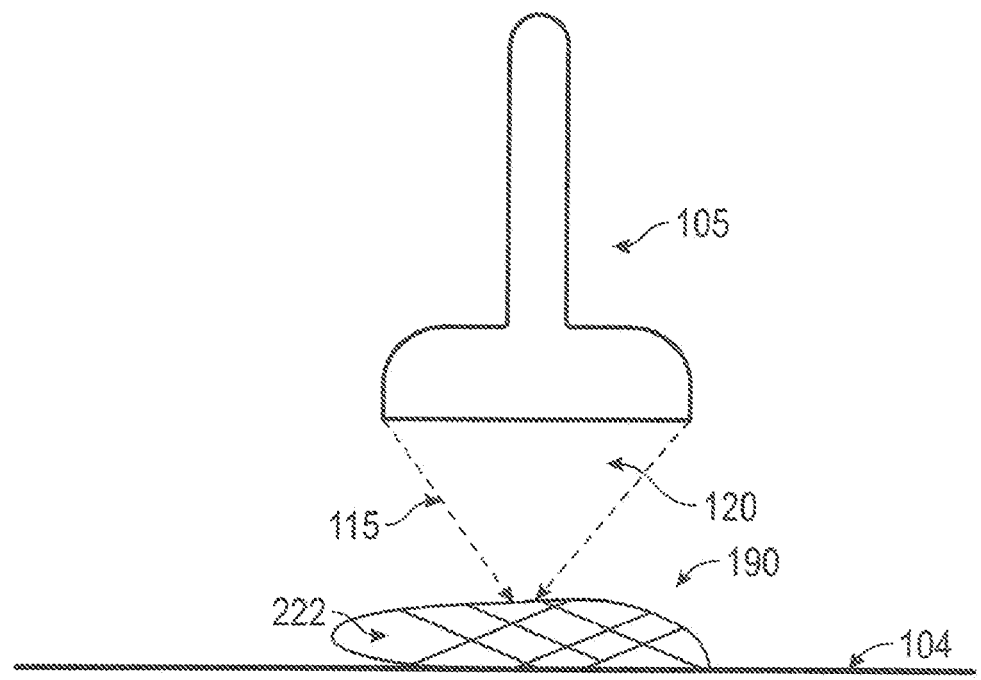
FIG. 7A illustrates various steps of a method, according to various non-limiting embodiments.
Figure 7B:
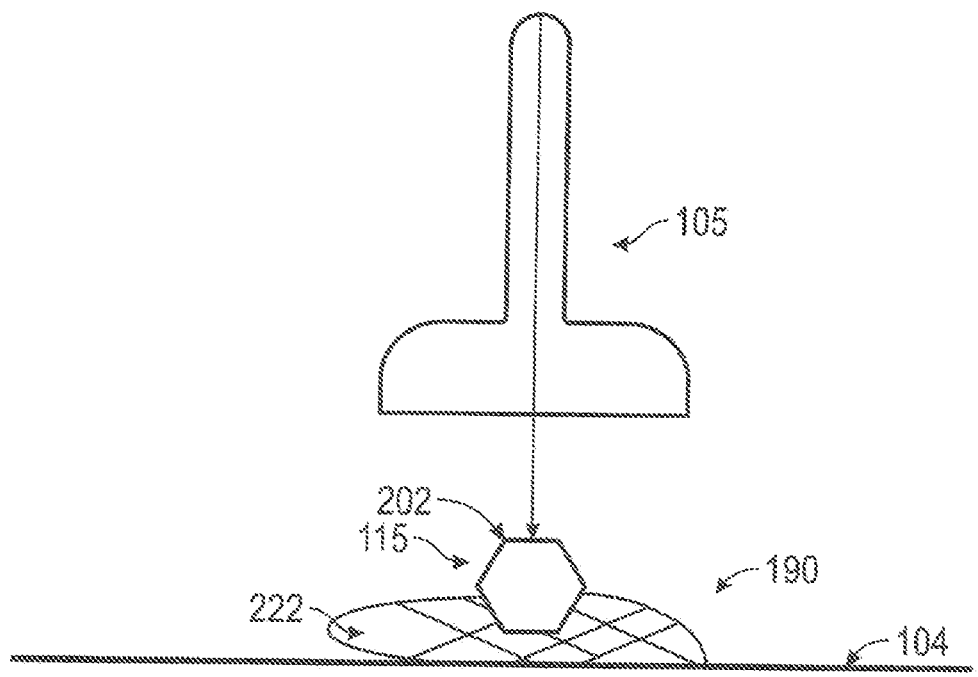
FIG. 7B illustrates various steps of a method, according to various non-limiting embodiments.
Figure 7C:
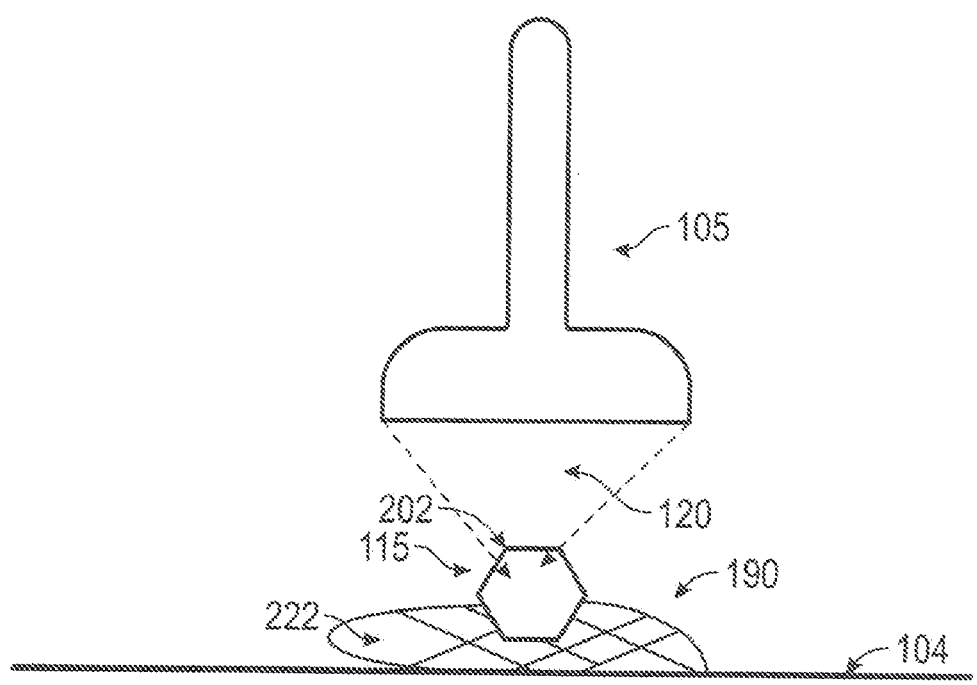
FIG. 7C illustrates various steps of a method, according to a various non-limiting embodiments.

Finally referring to FIGS. 7 A-C, method and apparatus for accelerating integration of implant onto a site are illustrated. According to various embodiments, implant 222 can be placed at site 190 on or slightly below surface 104. ROI 115 includes at least a portion of implant 222. In some embodiments, implant 22 is artificial skin. In some embodiments, probe 105 can optionally image site 190 (not shown). In some embodiments, probe 105 comprises a stand-off. In some embodiments, probe 105 comprises a lens. In some embodiments, probe comprises automated transducer motion mechanism to move transducer into a location to direct ultrasound energy 120 to site 190 on surface 104.

In various embodiments, ultrasound energy 120 is directed to at least one of site 190 and implant 222. In some embodiments, ultrasound energy 120 can ablate a portion of site 190. In some embodiments, ultrasound energy 120 can be focused to a portion of site 190. In some embodiments, ultrasound imaging 120 can create a lesion in a portion of site 190. In some embodiments, ultrasound energy can coagulate a portion of site 190.

According to various embodiments, needle 230 can be inserted through surface 104 and employed to direct medicant 202 to at least one of site 190 and implant 222. In other embodiments, ultrasound energy can create a pressure gradient to direct medicant 202 on surface 104 to at least one of site 190 and implant 222. In various embodiments, ultrasound energy 120 is directed to at least one of site 190 and implant 222. In some embodiments, ultrasound energy 120 can ablate a portion of site 190. In some embodiments, ultrasound energy 120 can be focused to a portion of site 190. In some embodiments, ultrasound energy 120 can weld implant 222 portion of site 190. In some embodiments, ultrasound energy 120 increases blood perfusion to site 190. In some embodiments, ultrasound energy accelerates inflammation peaking which may stimulate healing at site 190. In some embodiments, ultrasound energy 120 activates medicant 202. In some embodiments, medicant 202 is coated on at least a portion of implant 222. In such embodiments, ultrasound energy activates medicant 202 that is coated on implant 222.

According to various embodiments, a method can include targeting micro-tears within site 190, directing ultrasound energy 120 to the micro-tears within site 190, ablating at least a portion of the micro-tears, and improving the micro-tears within site 190. In some embodiments, the method further includes placing or directing a medicant into an area that includes at least a portion of the micro-tears within site 190. The directing ultrasound energy 120 to the micro-tears within site 190 can be before, during and/or after the placing or directing a medicant into an area that includes at least a portion of the micro-tears within site 190.

The following patents and patent applications are incorporated by reference: US Patent Application Publication No, 20050256406, entitled "Method and System for Controlled Scanning, Imaging, and/or Therapy" published Nov. 17, 2005; US Patent Application Publication No. 20060058664, entitled "System and Method for Variable Depth Ultrasound Treatment" published Mar. 16, 2006; US Patent Application Publication No, 20060084891, entitled "Method and System for Ultra-High Frequency Ultrasound Treatment" published Apr. 20, 2006; U.S. Pat. No. 7,530,958, entitled "Method and System for Combined Ultrasound Treatment" issued May 12, 2009; US Patent Application Publication No. 2008071255, entitled "Method and System for Treating Muscle, Tendon, Ligament, and Cartilage Issue" published Mar. 20, 2008; U.S. Pat. No. 6,623,430, entitled "Method and Apparatus for Safely Delivering Medicants to a Region of Tissue Using Imaging, Therapy, and Temperature Monitoring Ultrasonic System", issued Sep. 23, 2003; U.S. Pat. No. 7,571,336, entitled "Method and System for Enhancing Safety with Medical Peripheral Device by Monitoring if Host Computer is AC Powered" issued Aug. 4, 2009; US Patent Application Publication No. 20080281255, entitled "Methods and Systems for Modulating Medicants Using Acoustic Energy" published Nov. 13, 2008; US Patent Application Publication No. 20060116671, entitled "Method and System for Controlled Thermal Injury of Human Superficial Tissue," published Jun. 1, 2006; US Patent Application Publication No. 20060111744, entitled "Method and System for Treatment of Sweat Glands," published May 25, 2006; US Patent Application Publication No. 20080294073, entitled "Method and System for Non-Ablative Acne Treatment and Prevention," published Oct. 8, 2009; U.S. Pat. No. 8,133,180, entitled "Method and System for Treating Cellulite," issued Mar. 13, 2012; U.S. Pat. No. 8,066,641, entitled "Method and System for Photoaged Tissue," issued Nov. 29, 2011; U.S. Pat. No. 7,491,171, entitled "Method and System for Treating Acne and Sebaceous Glands," issued Feb. 17, 2009; U.S. Pat. No. 7,615,016, entitled "Method and System for Treating Stretch Marks," issued Nov. 10, 2009; and U.S. Pat. No. 7,530,356, entitled "Method and System for Noninvasive Mastopexy," issued May 12, 2009.

It is believed that the disclosure set forth above encompasses at least one distinct invention with independent utility. While the invention has been disclosed in the various embodiments thereof as disclosed and illustrated herein are not to be considered in a limiting sense as numerous variations are possible. The subject matter of the inventions includes all novel and non-obvious combinations and sub combinations of the various elements, features, functions and/or properties disclosed herein.

Various embodiments and the examples described herein are one and not intended to be limiting in describing the fall scope of compositions and methods of this invention. Equivalent changes, modifications and variations of various embodiments, materials, compositions and methods may be made within the scope of the present invention, with substantially similar results.

The invention claimed is:

1. A method of enhancing a cosmetic implant, the method comprising:
   targeting a location of the cosmetic implant in a patient;
   determining an enhancement necessary to improve an aesthetic of the cosmetic implant;
   delivering ultrasound energy to at least one of the cosmetic implant and tissue surrounding the cosmetic implant;
   improving the aesthetic of the cosmetic implant with the ultrasound energy, wherein the cosmetic implant is a breast implant located in a breast of the patient, the method further comprising:
   creating a conformal region of elevated temperature in at least one of the breast implant and tissue surrounding the breast implant;
   creating at least one lesion in the tissue surrounding the breast implant;
   applying mechanical ultrasound energy to at least one of the breast implant and the tissue surrounding the breast implant;
   moving the breast implant into a space created by the at least one lesion; and
   modifying a shape of the breast of the patient.

2. The method according to claim 1, wherein the improving the aesthetic of the cosmetic implant with the ultrasound energy is modifying a shape of the breast of the patient.

3. A method of enhancing an aesthetic of a breast of a subject, the method comprising:
   targeting a location of a desired aesthetic improvement of the breast;
   determining an enhancement necessary to produce the desired aesthetic improvement;
   delivering ultrasound energy to tissue within the breast at the location of the desired aesthetic improvement, the ultrasound energy creating at least one lesion in the location;
   applying mechanical ultrasound energy to at least one of the location of the desired aesthetic improvement or tissue surrounding the location of the desired aesthetic improvement moving the tissue surrounding the location of the desired aesthetic improvement into a space created by the at least one lesion;
   modifying a shape of the breast of the patient; and
   improving the aesthetic of the breast with the ultrasound energy.

4. The method of claim 3, wherein the improvement in the aesthetic of the breast with the ultrasound energy is the modifying the shape of the breast of the patient.

5. The method of claim 3, the method further comprising creating a conformal region of elevated temperature in the location of the desired aesthetic improvement of the breast.

6. A method of enhancing an aesthetic of a breast of a subject, the method comprising:
   targeting a location of a desired aesthetic improvement of the breast;
   determining an enhancement necessary to produce the desired aesthetic improvement;
   delivering focusing ultrasound energy to at least one of the location of the desired aesthetic improvement and tissue surrounding the location;
   creating at least one lesion in the location;
   applying mechanical ultrasound energy to at least one of the location of the desired aesthetic improvement or tissue surrounding the location of the desired aesthetic improvement moving the tissue surrounding the location of the desired aesthetic improvement into a space created by the at least one lesion;
   modifying a shape of the breast of the patient; and
   improving the aesthetic of the breast with the ultrasound energy.

7. The method of claim 6, wherein the improving the aesthetic of the breast with the focused ultrasound energy is the modifying the shape of the breast of the subject.

8. The method of claim 6, further comprising creating a conformal region of elevated temperature in the location of the desired aesthetic improvement of the breast.

* * * * *